United States Patent [19]

Heynen et al.

[11] Patent Number: 4,720,189

[45] Date of Patent: Jan. 19, 1988

[54] EYE-POSITION SENSOR

[75] Inventors: Jan Heynen, Ottawa; David A. Kahn, Nepean, both of Canada

[73] Assignee: Northern Telecom Limited, Montreal, Canada

[21] Appl. No.: 816,787

[22] Filed: Jan. 7, 1986

[51] Int. Cl.$^4$ ............................................. A61B 3/14
[52] U.S. Cl. .................................................. 351/210
[58] Field of Search ............................. 351/209, 210; 250/203 R

[56] References Cited

U.S. PATENT DOCUMENTS 3,507,988  4/1970  Holmes .
3,724,932  4/1973  Cornsweet et al. .
4,513,317  4/1985  Ruoff .

OTHER PUBLICATIONS

"Eye-Controlled Communication Aids" by J. H. ten Kate et al., Medical Progress Through Technology 8:1–21, Springer-Verlag, 1980.

Primary Examiner—Rodney B. Bovernick

[57] ABSTRACT

An eye-position sensor for use in an eye-activated optical transducer in which a spatial filter is used to modify light reflected from the eye to form a substantially rectangular pattern on a quadrantal array of contiguous sensors. This arrangement provides a substantially linear change in the output signal from the sensors in response to an equivalent movement of the eye.

7 Claims, 5 Drawing Figures

EYE-POSITION SENSOR

This invention relates to an eye-position sensor and more particularly to one that may be used in an eye-activated optical transducer which functions as a keyboard emulator for controlling such devices as a printer, monitor, or telephone modified with an eye-activated dialler and voice synthesizer.

BACKGROUND OF THE INVENTION

Certain severely handicapped people can only reliably communicate through their eye movements. To facilitate this communication, typewriting devices have been developed which utilize eye-position control. An example of such a system is described in an article entitled "Eye-Controlled Communication Aids" by J. H. ten Kate et al., Medical Progress Through Technology 8:1-21, Springer-Verlag 1980. Eye tracking or positioning devices have also been described in U.S. Pat. No. 3,507,988 entitled "Narrow-Band, Single-Observer, Television Apparatus" by William S. Holmes, issued Apr. 21, 1970; U.S. Pat. No. 3,724,932 entitled "Eye Tracker And Method" by Tom N. Cornsweet et al issued Apr. 3, 1973. Reference to eye tracking devices is also made in U.S. Pat. No. 4,513,317 entitled "Retinally Stabilized Differential Resolution Television Display" by Carl F. Ruoff, issued Apr. 23, 1985. In general, these devices use a photo-sensor which detects the change in diffused or specular infrared reflections from the eye as it moves. A limiting factor in the detection of eye movements for communication purposes is the non-linearity of the transducer. As a result, eye tracking calibration has often been difficult, time consuming and inconsistent.

STATEMENT OF THE INVENTION

It has been discovered that a substantially linear analog signal output can be obtained from an eye-position sensor by utilizing optical componentry including a point source of light and a spatial filter between the eye and a quadrantal array of contiguous sensors so as to cast a substantially rectangular pattern of light on the sensors from the specularly reflected infrared light. With such an arrangement the eye acts as a convex mirror to reflect an image of the point source onto the sensor rather than an image of the eye itself.

In accordance with the present invention there is provided an eye-position sensor which provides signals representative of the X and Y coordinates of light reflected from the cornea of the eye. The sensor comprises a substantially point source of light for illuminating the eye and a light sensor which includes a quadrantal array of contiguous photo detectors each of which generates a signal which is proportional to its illuminated area. Also included is a lens for collimating the light from the point source of light reflected from the cornea of the eye onto the quadrantal array of contiguous photo detectors. The sensor also includes a spatial filter for shaping the distribution of light reflected from the eye to provide a rectangular pattern of light on the array. The spatial filter is oriented so that each corner of the rectangular pattern lies in a different quadrant of the array. The filter is disposed so that movement of the eye changes the position of the pattern illuminating the array. In a particular embodiment each of the photodetectors has a substantially square sensing surface, the size of which is preferably the same as that of the pattern being cast on the array.

BRIEF DESCRIPTION OF THE DRAWINGS

An example embodiment of the invention will now be described with reference to the accompanying drawings in which.

DESCRIPTION OF THE PREFERRED EMBODIMENT

Figure 1:
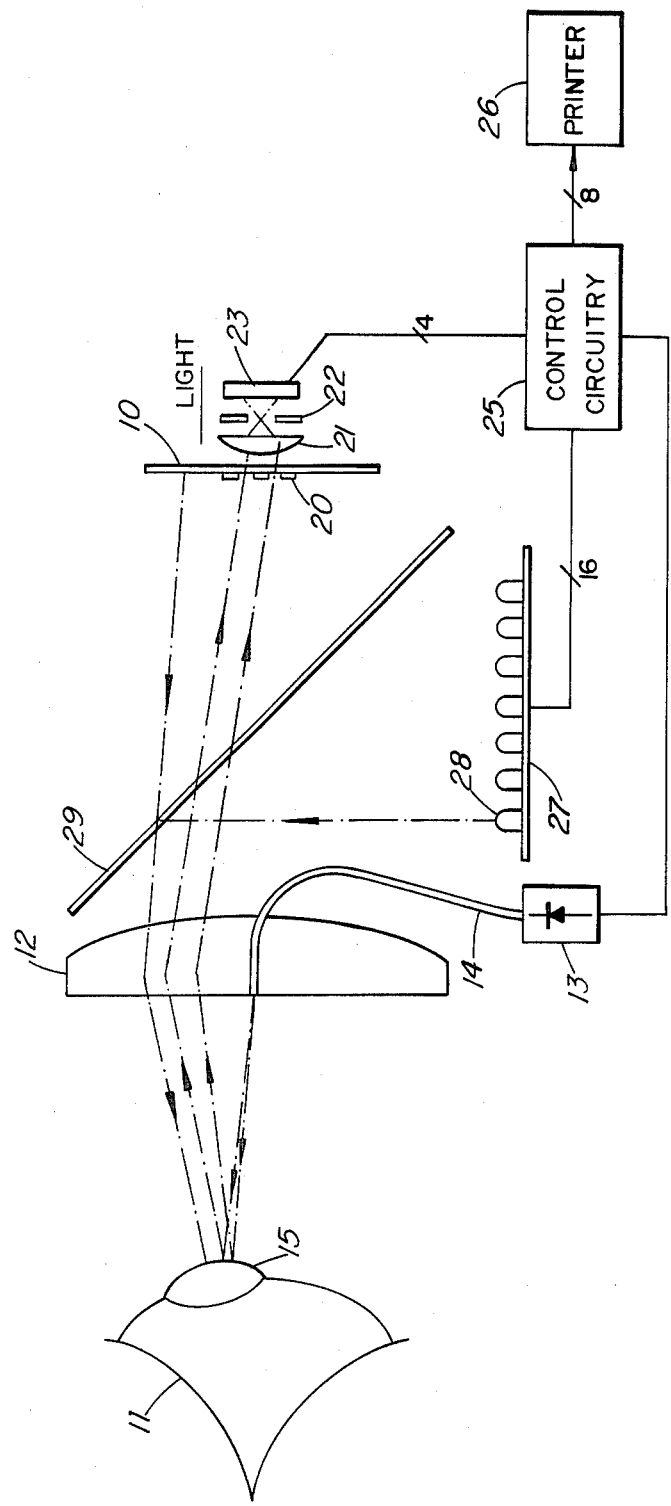
FIG. 1 illustrates an eye-position sensor in accordance with the present invention.
Figure 2:
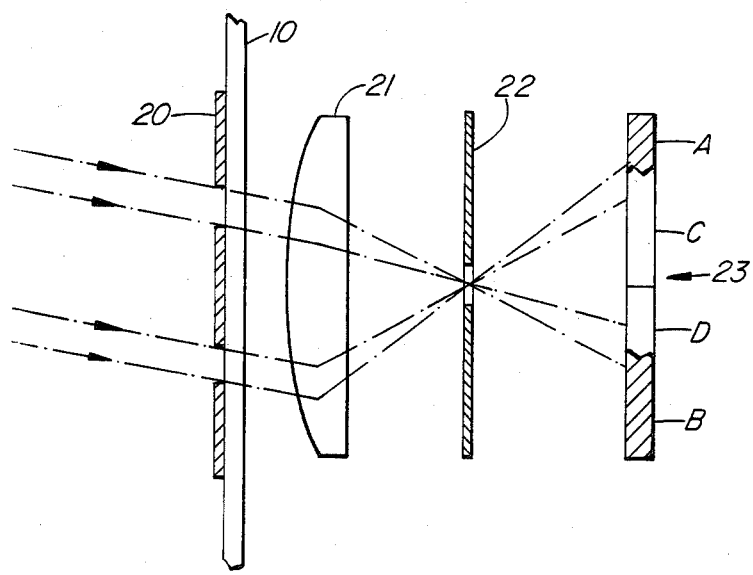
FIG. 2 illustrates an enlarged portion of the eye-position sensor illustrated in FIG. 1.

Referring to FIGS. 1 and 2, the eye-position sensor comprises a translucent alpha-numeric character display pad 10 in which the characters are illuminated e.g. by ambient light. The entire structure which is contained in a housing (not shown) can be positioned so that the eye 11 of a user such as a severely handicapped person, is focussed on the display pad 10 through a 34 millimeter diameter plastic lens 12 which is positioned a distance approximately equal to its focal length of 37.5 millimeters from the eye 11, less the virtual image distance behind its cornea 15. This distance ensures that the reflected rays which have passed through the lens 12 emerge substantially collateral. A light emitting diode LED) 13 transmits 10 microwatts of infrared light at an 820 nanometer wavelength. The infrared light is coupled from the light-emitting diode (LED) 13 through the lens 12 by an optical fiber 14, where it is transmitted towards the eye 11. The diameter of the illuminated area of the eye 11 from the infrared light from the fiber 14 is restricted by the beam spread to about 6 millimeters. This aids the sensitivity of the system.

Figure 4:
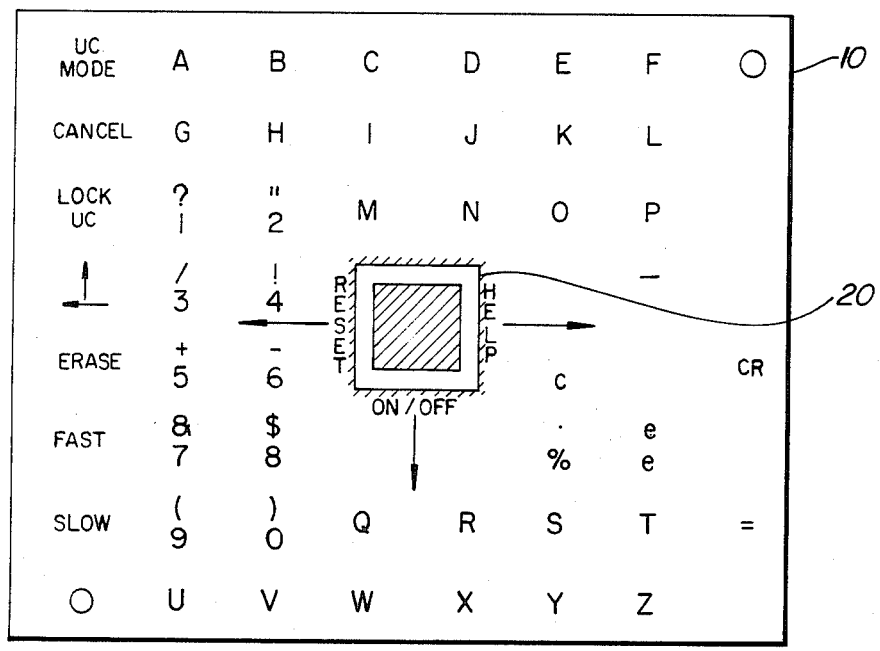
FIG. 4 illustrates a translucent character display and a spatial filter which forms part of the eye-position sensor illustrated in FIG. 1.

When the eye 11 of the user is focussed on one of the characters of the character display pad 10, light from the infrared source 13 is reflected from the cornea 15 of the eye 11 through the lens 12 to a spatial filter 20 having a square annular shape with overall dimensions of 3 millimeters and an annular thickness of 1 millimeter as shown in more detail in FIG. 4. The infrared light reflected from the eye 11 which passes through this filter 20 is then coupled through a 6 millimeter focal length plastic lens 21. After passing through a window aperture 22 which is used to exclude extraneous light, the reflected light is detected by a light sensor 23.

The lens 21 is used to concentrate the light from the filter 20 onto the sensor 23. The aperture 22 may be used to attaenuate unwanted reflections. If sufficient reflected light is available the elements 21 and 22 may be eliminated so that the light passing through the filter 20 falls directly on the sensor 23. Also the relative position of the filter 20 and lens 21 can be reversed. The filter 20 provides two significant advantages. By restricting the light illuminating the sensor 23 to a square pattern, its response to eye movement is substantially linear. Also the filter 20 attenuates diffuse reflections from other parts of the eye 11. In some instances such reflections may be focussed in the center of the pattern. By utilizing an annular shaped filter, this center portion is blocked thereby further improving the response characteristics.

Figure 3:
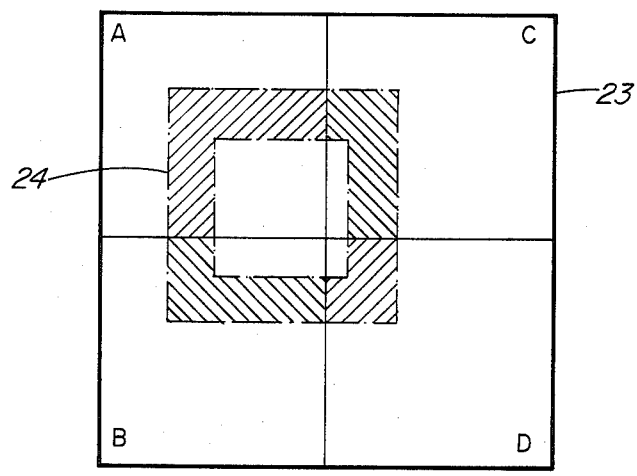
FIG. 3 illustrates a light sensor which forms part of the eye-position sensor illustrated in FIG. 1.

As shown in FIG. 3, the light sensor 23 comprises a quadrantal array of contiguous photo detectors A, B, C, and D, each of which generates a signal current which is proportional to the illuminated area. The distance between the lens 21 and the surface of the sensor 23 is such that a defocussed square annulus of light 24 from the spatial filter 20 is cast thereon. Because the illuminated area 24 is square and oriented in the same direction as the axes of the sensors 23, a horizontal X or vertical Y movement of the image will result in a substantially linear change in the output signal current from each of the photo detectors A, B, C, and D. The signals from the four quadrants A, B, C, and D of the sensor 23 are coupled to control circuitry 25 which processes the signal so as to generate standard ASCII characters for controlling a printer 26. Concurrently, the control circuitry 25 powers a selected one 28 of an 8×8 matrix of LEDs 27. The light from the one illuminated LED 28 is reflected from a beam splitter 29, disposed between the display panel 10 and the lens 12, to the eye 11. The matrix of LEDs 27 is disposed so that the selected LED 28 provides virtual highlighting of the alpha-numeric character on the display pad 10 on which the eye 11 is currently focussed.

Figure 5:
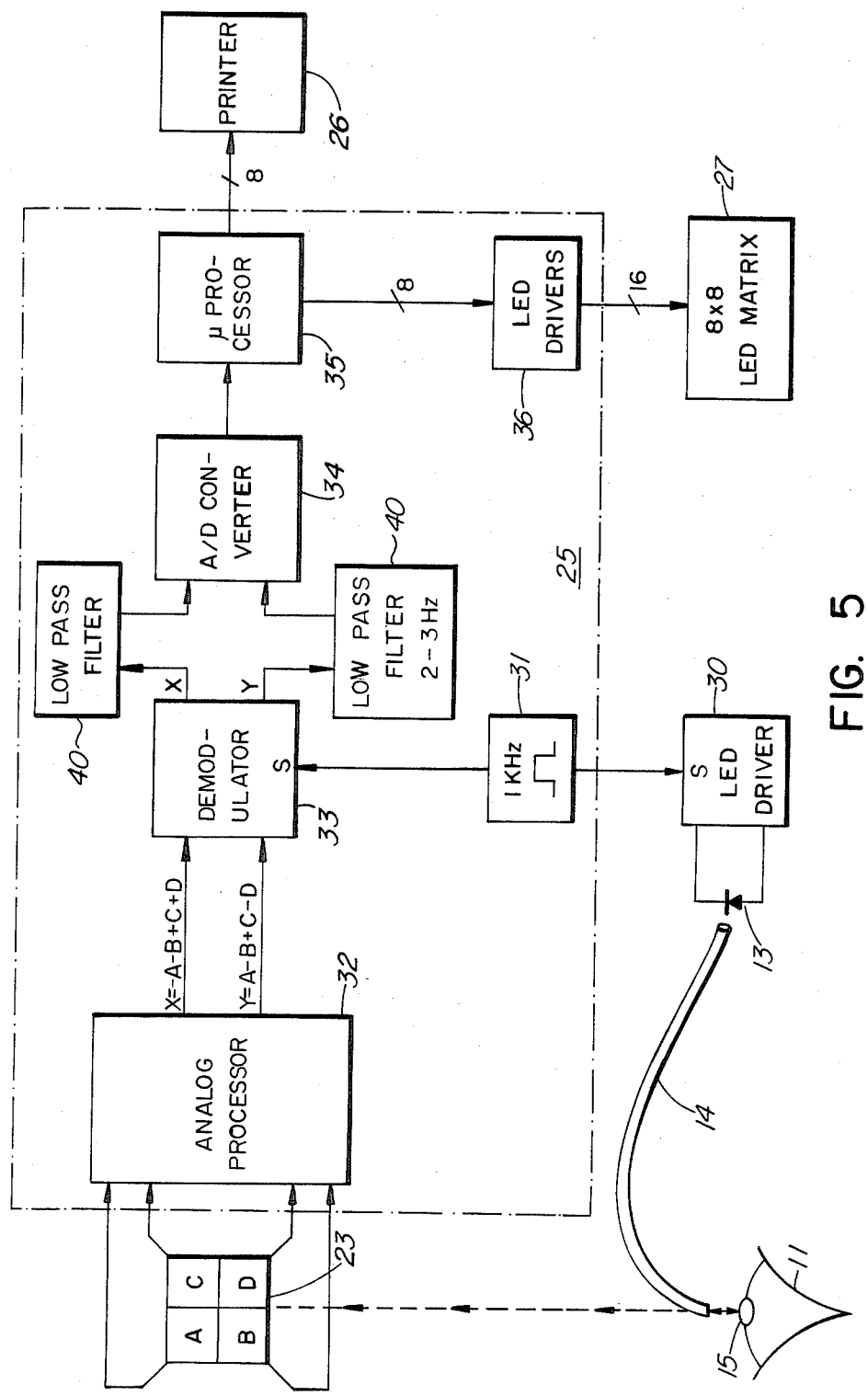
FIG. 5 illustrates in further detail control circuitry which forms part of the eye-position sensor illustrated in FIG. 1.

Referring to FIG. 5, infrared light is coupled from the LED 13 through the optical fiber 14 where it is transmitted so as to illuminate the eye 11. The LED 13 is remote from the light sensor 23 to prevent electrical interference from the modulated drive current generated by a LED driver 30 which switches the LED on and off at a 1 kHz rate under control of a 1 kHz oscillator 31 in the control circuit 25. The use of a modulated signal permits the use of a high gain low noise amplifier at the input to the control circuit 25, and substantial freedom from room lighting interference.

As explained previously, the infrared light reflected from the cornea 15 of the eye 11 generates four electrical signal currents A, B, C, and D, on the four quadrant light sensor 23. These signal currents are proportional to the incident light on them. The electrical signal currents from the sensor 23 are amplified and processed in an analog signal processor 32 which generates horizontal X and vertical Y coordinate voltages such that $X=C+D-A-B$ and $Y=A+C-B-D$. These two signals X and Y are then coupled to a multiplexing A/D converter 34 through synchronous demodulators 33 and low pass filters 40. The demodulators 33 are driven by the 1 Khz oscillator so that their output is in synchronization with that of the output from the LED 13 to produce output signals which are then digitized in the 8-bit analog-to-digital (A/D) converter 34. The 3 Hz low pass filters 40 ensure that the control circuit 25 will respond only to eye movements. The output of the converter 34 is fed to a microprocessor 35 which generates the standard 8-bit ASCII coded signals which are fed to the printer 26. Through an LED driver 36 the selected character is given virtual highlighting through the 8×8 LED matrix 27.

One feature of the present system is the coaxiality of the illuminating radiation from the fiber 14 end, the axis of the photosensor array 23 and the axis of the display pad 10. When the eye 11 is gazing at the center of the display pad 10, the incident and reflected radiation are coaxial. This permits the system to respond in comparable fashion to both horizontal X and vertical Y movements. Non-coaxial systems as described in the prior art, react very differently to the two directions of movement. One example of these systems is described in "An Ocular Control Device For Use By The Severely Handicapped", by G. A. Rinard, and D. E. Rugg, 1976 Conference on Systems and Devices for the Diabled, Boston, Mass. June 1976. Another example is described by K. C. Anderson et al in "An Eye Position Controlled Typewriter" Digest 11th International Conference Med. Biol. Eng. 29:410-411, 1976.

Utilizing the LED matrix 27, the present system provides immediate feedback to the user as to where the eye is focussed as determined by the system. When the display pad 10 is illuminated by ambient light from the front or back, black characters on a translucent white background are seen. The confirmatory illumination from the LED matrix 27 is a colour (typically red or green) so that the user can readily adapt to the system when the latter is not accurate in its selection. For example, if the illuminated character is one space to the right of the character being focussed on, the user may shift his gaze by one space to the left thus achieving his desired choice. The angular distance between characters is approximately 4 degrees and both positions are well within the visual span of the static eye.

Character selection is completed by the expiration of a dwell time period typically in the order of one second. After the dwell time has expired, control circuitry within the microprocessor 35 produces a sound on a loudspeaker or buzzer (not shown) to indicate the need for a next character selection. Alternatively, when the user has some elementary muscle control, he may be able to activate a switch to complete the selection.

The display pad 10 contains a rest space in its center. When the eye 11 gazes at this space the system takes no action and the user may ponder his next move without interference. Once the system is installed, electronic calibration under control of the microprocessor 35, is achieved by the user gazing at a sequence of flashing lights located in the four corners of the display pad 10. The processed signal voltages modify the digital output of the microprocessor 35 to match the characteristics of the operator's eye and his exact eye position in reference to the optical sensor 23.

In an alternative embodiment, the LED matrix 27 may be located directly behind the display pad 10 while the infrared source, from the output of the fiber 14, may be in the position shown in the drawings for the LED matrix 27. This may be altered further so that the output end of the fiber 14 and the detectors 23 are interchanged. In each case however the spacial filter 20 is utilized to provide the square pattern of light on the photo detectors 23. With either of these alternative embodiments, unwanted reflections of infrared light from the lens 12 may occur. These may be reduced by angling the axis of the lens 12 about 6 degrees or by adding anti-reflective coating to the lens. In all embodiments however, it is important that the housing for the structure be held steady with respect to the eye such as by using a glasses frame and/or elastic strap, in conjunction with the bridge of the nose.

What is claimed is:

1. In an eye-position sensor which provides a signal representative of the X and Y coordinates of light reflected from the cornea of an eye;
  said eye-position sensor comprising:
    a substantially point source of light for illuminating the eye; and a light sensor including:

a quadrantal array of contiguous photo detectors each of which generates a signal which is proportional to the illuminated area thereof;

a lens for collimating the light from the point source of light reflected from the cornea of the eye, onto the quadrantal array of contiguous photo detectors;

said light sensor characterized by:

a spatial filter for providing a substantially rectangular pattern of light from said source which is specularly reflected from the eye onto the array so that each corner of the rectangular pattern lies in a different quadrant of the array;

the filter being disposed so that movement of the eye changes the position of the pattern illuminating the array.

2. An eye-position sensor as defined in claim 1 in which the light sensor is further characterized by:

each of the photodetectors has a sensing surface of a size at least as great as the substantially rectangular pattern of light which is incident thereon.

3. An eye-position sensor as defined in claim 2 in which the pattern of light from the filter is a substantially square annulus of light having substantially the same orientation as that of the array.

4. An eye-position sensor as defined in claim 3 which additionally comprises:

a display panel having an array of characters thereon;

said lens is disposed between the display panel and the eye for focusing the eye on the characters;

a partial light reflecting surface disposed between the lens and the display panel; and an array of lights which produces a virtual image from reflections from the partial light reflecting surface;

the virtual image of each one of the array of lights being superimposed on respective ones of each of the characters on the display panel as seen by the eye to provide highlighting thereof.

5. An eye-position sensor as defined in claim 4 in which the point source of light is disposed in the middle of the lens, and the light sensor is disposed in the middle of the display panel, and in which the light sensor is further characterized by:

a further lens disposed between the spatial filter and the quadrantal array to condense the specularly reflected infrared light on the array.

6. An eye-position sensor as defined in claim 5 further comprising:

an aperture disposed between the further lens and the array for limiting spurious reflections from reaching said array.

7. An eye-position sensor as defined in claim 4 further comprising:

control means responsive to the signals from each of the photo sensors for illuminating one of the array of lights to produce a virtual image which is aligned with the character on the display board on which the eye is focused.

* * * * *